United States Patent
Hatten et al.

(10) Patent No.: US 10,370,685 B2
(45) Date of Patent: *Aug. 6, 2019

(54) PROCESSES FOR CONTROLLING THE CONCENTRATION OF CO-PRODUCED OXYGENATED ORGANICS IN ANAEROBIC FERMENTATION BROTHS FOR THE BIOCONVERSION OF SYNGAS TO PRODUCT OXYGENATED ORGANIC COMPOUND

(71) Applicant: Synata Bio, Inc., Warrenville, IL (US)

(72) Inventors: Chad Hatten, Naperville, IL (US); Robert Hickey, Okemos, MI (US)

(73) Assignee: Synata Bio, Inc., Warrenville, IL (US)

( * ) Notice: Subject to any disclaimer, the term of this patent is extended or adjusted under 35 U.S.C. 154(b) by 636 days.

This patent is subject to a terminal disclaimer.

(21) Appl. No.: 14/327,370

(22) Filed: Jul. 9, 2014

(65) Prior Publication Data

US 2016/0010123 A1    Jan. 14, 2016

(51) Int. Cl.

| | |
|---|---|
| *C12P 7/54* | (2006.01) |
| *C12P 7/06* | (2006.01) |
| *C12P 7/16* | (2006.01) |
| *C12P 7/52* | (2006.01) |
| *C12P 7/04* | (2006.01) |

(52) U.S. Cl.
CPC .............. *C12P 7/54* (2013.01); *C12P 7/04* (2013.01); *C12P 7/06* (2013.01); *C12P 7/065* (2013.01); *C12P 7/16* (2013.01); *C12P 7/52* (2013.01); *Y02E 50/10* (2013.01); *Y02E 50/17* (2013.01); *Y02P 20/582* (2015.11)

(58) Field of Classification Search
CPC .............................................. C12P 7/14
See application file for complete search history.

(56) References Cited

U.S. PATENT DOCUMENTS

| | | | | |
|---|---|---|---|---|
| 2009/0203100 A1* | 8/2009 | Simpson | ................... | C12P 7/14 435/161 |
| 2010/0227377 A1* | 9/2010 | Adams | ..................... | C12N 1/20 435/252.7 |

\* cited by examiner

*Primary Examiner* — Bin Shen
(74) *Attorney, Agent, or Firm* — Cardinal Law Group

(57) ABSTRACT

Processes are disclosed for economically and effectively removing co-produced oxygenated organic compound from an anaerobic, aqueous fermentation broth used for the bioconversion of syngas to product oxygenated organic compound. The processes involve subjecting a portion of the aqueous fermentation broth after recovery of the product oxygenated organic compound to anaerobic organic bioconversion, and recycling the broth for use in the bioconversion of syngas.

16 Claims, 1 Drawing Sheet

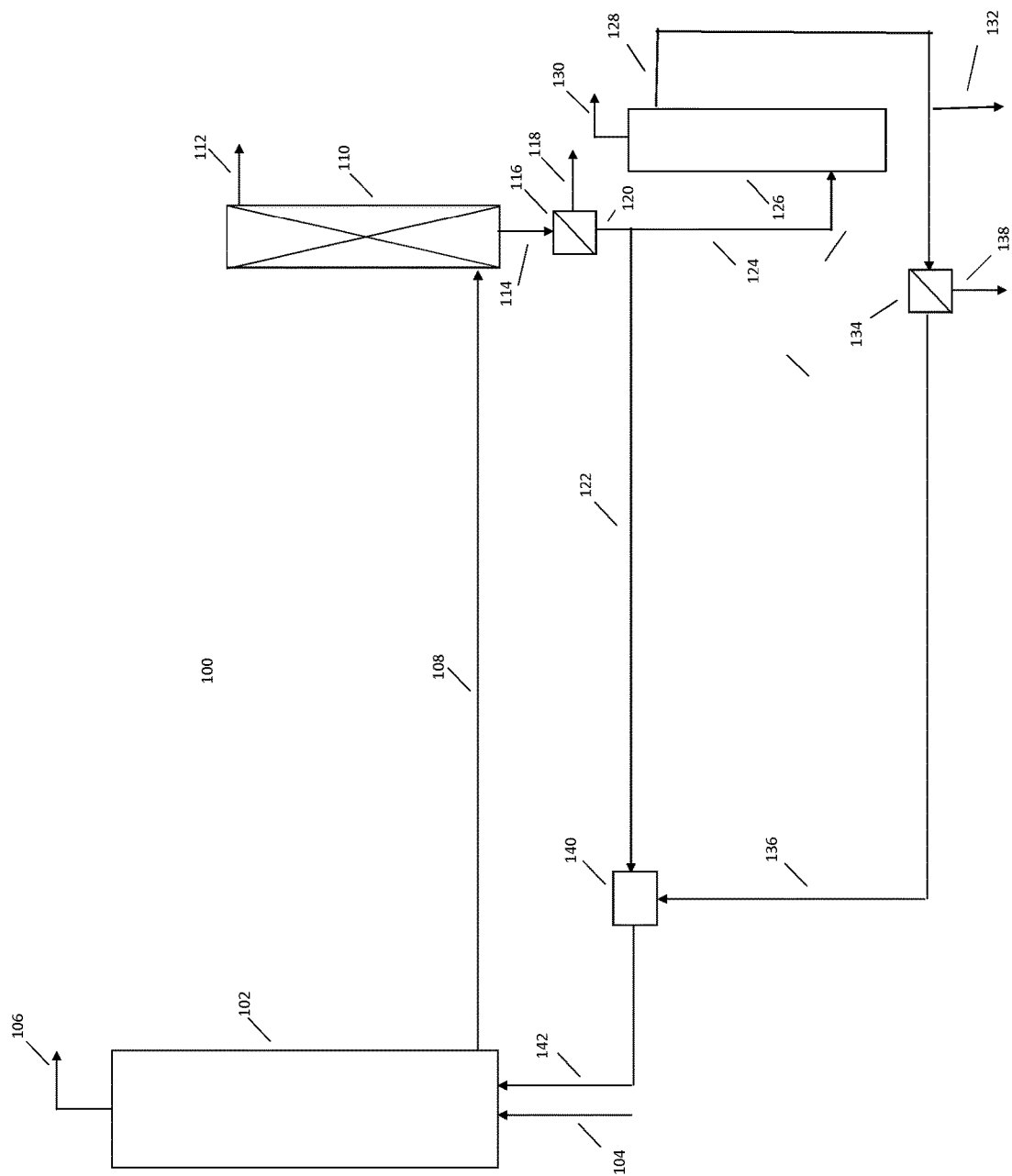

PROCESSES FOR CONTROLLING THE CONCENTRATION OF CO-PRODUCED OXYGENATED ORGANICS IN ANAEROBIC FERMENTATION BROTHS FOR THE BIOCONVERSION OF SYNGAS TO PRODUCT OXYGENATED ORGANIC COMPOUND

FIELD OF THE INVENTION

This invention pertains to processes for controlling the concentration of co-produced oxygenated organics from anaerobic aqueous fermentation broths used for the bioconversion of syngas to product oxygenated organic compound.

BACKGROUND

Anaerobic fermentations of hydrogen and carbon monoxide involve the contact of a gaseous substrate-containing feed with an aqueous fermentation broth containing microorganisms capable of generating oxygenated organic compounds such as ethanol, acetic acid, propanol and n-butanol. The bioconversion of carbon monoxide results in the production of oxygenated organic compound and carbon dioxide. The conversion of hydrogen involves the consumption of hydrogen and carbon dioxide, and this conversion is sometimes referred to as the $H_2/CO_2$ conversion or, as used herein, the hydrogen conversion.

Typically the substrate gas for carbon monoxide and hydrogen conversions is, or is derived from, a synthesis gas (syngas) from the gasification of carbonaceous materials, from the reforming of natural gas and/or biogas from anaerobic digestion or from off-gas streams of various industrial methods. The gas substrate contains carbon monoxide, hydrogen, and carbon dioxide and usually contains other components such as water vapor, nitrogen, methane, ammonia, hydrogen sulfide and the like. For the sake of convenience, the substrate gas is referred to herein as "syngas" even though it may only contain one of carbon monoxide and hydrogen and may not be derived by the gasification of carbonaceous materials.

These anaerobic fermentation processes are suitable for continuous processes. The syngas is passed into a bioreactor the aqueous fermentation broth for the bioconversion. Off gases can be removed from the bioreactor, and aqueous broth can be withdrawn from the bioreactor for recovery of the oxygenated organic compound at a rate sufficient to maintain steady-state operation. For the anaerobic fermentations to be commercially viable, economies of scale are required. Hence, commercial scale reactors, i.e., those with liquid capacities of at least 1 million, and more often at least about 5, say, 5 to 25, million, liters would be advantageous.

Continuous syngas fermentation processes typically produce co-produced oxygenated organic compounds in addition to the sought, product oxygenated organic compound. The co-produced oxygenated organic compounds can be co-metabolites that are not desired or intermediate metabolites in the bio-production of the sought, product oxygenated organic compound. Also, co-produced oxygenated organic compounds can be produced by contaminating, or adventitious, microorganisms present in the aqueous fermentation broth. In some instances, these co-produced oxygenated organic compounds may be produced at rates, relative to the production rate of the sought, product oxygenated organic compound, that cause a build-up of the co-produced oxygenated organic compound in the aqueous broth. This build-up of the co-produced oxygenated organic compound is particularly untoward where the co-produced oxygenated organic compound reaches concentration levels that are inhibitory or toxic to the microorganisms used for the syngas fermentation. In some other instances, the co-produced oxygenated organic compound, when at sufficient concentrations, can adversely affect the metabolic pathways of certain microorganisms used for the bioconversion of syngas. For instance, where an alcohol is the sought, product oxygenated organic compound, with some microorganisms, the presence of certain concentrations of free carboxylic acids can induce a product distribution shift in which the microorganisms to generate a higher percentage of carboxylic acids. The exponentially increasing production of the acids leads to an increasing acidity in the fermentation broth causing an eventual loss of the microorganism being able to maintain cell membrane potential and loss of the population of microorganisms.

Although the fermentation broth could be discarded in the event that the concentration of the undesired organic compound becomes excessive, water, nutrients and dissolved substrate for the fermentation would also be lost. Additionally, for commercial-scale bioreactors, disposal of the large volume of aqueous broth in a bioreactor can be problematic depending upon the capacity of the waste water treatment system. Since a commercial-scale bioreactor may contain in excess of 1 million liters of aqueous broth, it is likely that the waste water from the bioreactor would have to be slowly discharged to the waste water treatment system to prevent exceeding capacity. Thus, the downtime of the affected bioreactor would be extended, resulting in a further loss of production. The amount of water lost could also be an economic loss.

In some instances, the undesired organic compound may be capable of being selectively removed such as by ion-exchange resins or membrane separations. These approaches may not provide suitable selectivity and are capital intensive yet may only be required sporadically or intermittently. But when needed, these unit operations must be able treat large quantities of fermentation broth in a short period of time. Moreover, they suffer from potential issues with fouling.

Accordingly, processes are sought for the removal of at least one undesired organic compound from an anaerobic fermentation broth that involve low capital expense.

SUMMARY OF THE INVENTION

By this invention processes are provided for economically and effectively controlling the concentration of one or more co-produced oxygenated organic compounds (referred to herein individually and collectively as the Adverse Component) in an anaerobic, aqueous fermentation broth used for the bioconversion of syngas to product oxygenated organic compound. The processes of this invention can avoid discarding the entire volume of aqueous fermentation broth due to unacceptable concentrations of Adverse Component occurring. Thus, loss of downtime, and lost production of product oxygenated organic compound, can be attenuated. Moreover, the processes of this invention do not require the undue loss or removal of nutrients or dissolved substrate from the broth.

The processes of this invention can be used on a continuous or intermittent basis to control the concentration of Adverse Component in the fermentation broth. The processes are suitable for small scale as well as commercial scale facilities for the production of product oxygenated organic compound. The syngas bioconversion processes to which this invention pertains are characterized as being continuous processes in which fermentation broth is continuously or intermittently withdrawn from a bioreactor assembly used for the syngas bioconversion for recovery of product oxygenated organic compound and at least a portion of the withdrawn fermentation broth, after having product oxygenated organic compound recovered therefrom, is returned to the bioreactor assembly. In accordance with the processes of this invention, a portion of the withdrawn fermentation broth is subjected to anaerobic organic bioconversion, and preferably high rate anaerobic organic bioconversion, prior to being recycled to the bioreactor assembly. The anaerobic organic bioconversion degrades the Adverse Component and provides a treated fermentation broth having a reduced concentration of Adverse Component. The portion of the withdrawn fermentation broth that is subjected to the anaerobic organic bioconversion is sufficient to maintain the concentration of the Adverse Component below that which would be unduly adverse to the microorganism population, e.g., would be inhibitory or toxic or would cause an increase in the production of Adverse Component as through a product distribution shift. Advantageously, the anaerobic organic bioconversion generates a biogas that contains methane and carbon dioxide. The methane can be used as an energy source or passed to, e.g., a reformer for conversion to syngas, and thus Adverse Component is converted into a useful product. Since the generated biogas contains carbon dioxide and potentially hydrogen sulfide and ammonia, all, or a portion of, the biogas can be passed to the aqueous fermentation broth used for the bioconversion of syngas. The portions may be aliquot portions or may have all or a portion of one or more components removed.

The processes can be practiced without additional undue capital expense.

Moreover, the processes do not necessarily pose the same type of fouling problems associated with the use of membranes or ion exchange resins to remove the Adverse Component. Because the processes of this invention only require a portion of the withdrawn fermentation broth being recycled to the bioreactor assembly after recovery of product oxygenated organic compound, nutrients and dissolved substrate are recycled to the bioreactor assembly.

In its broad aspects, the processes of this invention for controlling the concentration of at least one co-produced oxygenated organic compound in an anaerobic, aqueous fermentation broth used for bioconverting a gas substrate comprising carbon monoxide, hydrogen and carbon dioxide in the aqueous fermentation broth which contains microorganisms suitable for converting said substrate to product oxygenated organic compound, comprise:

a. continuously contacting said gas substrate with said aqueous fermentation broth in a bioreactor assembly, said broth being under acidic, anaerobic fermentation conditions, to bioconvert gas substrate to oxygenated organic compounds and provide a product oxygenated organic compound-containing broth and a depleted gas phase, said anaerobic fermentation conditions also producing a co-produced oxygenated organic compound;

b. continuously withdrawing the depleted gas phase from said aqueous broth;

c. continuously or intermittently withdrawing a portion of said broth for recovery of said product oxygenated organic compound, said withdrawal being sufficient to maintain the product oxygenated organic compound in said broth below a concentration that unduly adversely affects the microorganisms;

d. continuously separating at least one product oxygenated organic compound from a withdrawn portion of said broth to provide at least one fraction rich in said at least one product oxygenated organic compound and a depleted aqueous fraction containing said at least one co-produced oxygenated organic compound;

e. continuously recycling at least a portion of the depleted aqueous fraction to the bioreactor assembly; and f. continuously or intermittently subjecting a portion of the depleted aqueous fraction to anaerobic organic bioconversion prior to being recycled to the bioreactor assembly wherein the portion of the depleted aqueous fraction subjected to anaerobic organic bioconversion is sufficient to maintain the concentration of the at least one co-produced oxygenated organic compound below that which unduly adversely affects the microorganisms.

Those skilled in the art of syngas fermentation to produce product oxygenated organic compound will readily understand that the concentration of an Adverse Component that will unduly adversely affect the microorganisms will depend upon the microorganisms, the oxygenated organic compound and the fermentation conditions. An unduly adverse effect means that microorganisms are adversely affected by the concentration of the Adverse Component which results in a significantly reduced, e.g., reduced by at least 15 percent, conversion of carbon monoxide or hydrogen per gram of active cells per liter, all other conditions remaining the same. The occurrence of an unduly adverse effect is typically observed by assessing the specific activity rate, i.e., the mass bio-consumed per mass of active microorganism per unit time, which under steady-state conditions can be approximated by the overall conversion for the volume of aqueous fermentation broth in the reactor assembly.

Preferably, the concentration of the Adverse Component in the aqueous fermentation broth is maintained below about 90 percent of that which would adversely affect the microorganisms. Although very low concentration of Adverse Component can be maintained in the aqueous fermentation broth, in some preferred modes of operation a significant concentration of the Adverse Component is maintained in the aqueous fermentation broth, say, between about 10 and 75, and sometimes between about 25 and 75, percent of that which would adversely affect the microorganisms. The portion of the depleted aqueous fraction that is subjected to anaerobic organic bioconversion in step (f) can vary over a wide range but is sufficient to control the concentration of the Adverse Component in the aqueous fermentation broth. Usually less than about 50, say, about 5 to 50, and sometimes between about 5 and 25, volume percent of the depleted aqueous fraction is subjected to anaerobic organic bioconversion. Lower flow rates to the anaerobic organic bioconversion can reduce the size of the required equipment. The extent of bioconversion of the Averse Component being subjected to anaerobic organic bioconversion is also a factor affecting the concentration of the Adverse Component that is maintained in the aqueous fermentation broth. Frequently, the anaerobic organic bioconversion degrades at least about 75 mass percent, and preferably essentially all, of the Adverse Component contained in the portion of the depleted aqueous fraction subjected to the bioconversion.

In one mode of operation of the processes of this invention, the portion of the depleted aqueous fraction that is subjected to the anaerobic organic bioconversion is the primary variable in modulating the concentration of the Adverse Component in the aqueous fermentation broth. Any variation in the extent of conversion of the Adverse Component from the anaerobic organic bioconversion can be accommodated, if necessary, by altering the portion of the depleted aqueous fraction that is subjected to anaerobic organic bioconversion.

BRIEF DESCRIPTION OF THE DRAWING

The FIG. 1 is a schematic depiction of an apparatus that can be used in the practice of the processes of this invention.

DETAILED DISCUSSION

All patents, published patent applications and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous broth. The sought oxygenated organic compound from the bioconversion of syngas is referred to herein as product oxygenated organic compound or simply oxygenated organic compound unless the context is clear that it is referring to an Adverse Component.

The Adverse Component, i.e., co-produced oxygenated organic compound, is one or more metabolic products from the bioconversion of syngas which may be produced by the microorganism producing the product oxygenated organic compound or an adventitious microorganism. The Adverse Component comprises one or more oxygenated organic compounds other than the product oxygenated organic compound.

Anaerobic organic bioconversion is biodegradation of organic compounds by microorganisms in the absence of oxygen. The product of the organic bioconversion includes methane and carbon dioxide, and where amino acids are present, ammonia, and where sulfur compounds are present, hydrogen sulfide.

High rate anaerobic organic bioconversion is defined herein as anaerobic organic bioconversion where the hydraulic residence time to substantially eliminate the Adverse Component is less than about 30, preferably less than about 24, hours, and include anaerobic reactors such as anaerobic membrane-type reactors (operable to carry out membrane-type anaerobic organic bioconversion), attached growth-type reactors (operable to carry out attached growth-type anaerobic bioconversion) including anaerobic fluidized beds such as in expanded granule sludge bed and internal circulation bioreactors, anaerobic filters and upflow anaerobic sludge blanket-type bioreactors where the broth is passed upwardly through a blanket containing the digesting microorganisms and granules are formed which are dense biofilms, and hybrids and variants thereof.

A bioreactor assembly is an assembly of one or more vessels suitable to contain aqueous broth and microorganisms for the bioconversion and can contain associated equipment such as injectors, recycle loops, agitators, and the like.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

Fossil carbonaceous materials, or fossil fuels, include, but are not limited to, natural gas; petroleum including carbonaceous streams from the refining or other processing of petroleum including, but not limited to, petroleum coke; and lignite and coal.

Aqueous broth, or aqueous fermentation broth, means a liquid water phase which may contain dissolved compounds including, but not limited to hydrogen, carbon monoxide, and carbon dioxide. The broth may, but is not required, to contain microorganisms.

Intermittently means from time to time and may be at regular or irregular time intervals.

Syngas means a gas, regardless of source, containing at least one of hydrogen and carbon monoxide and may, and usually does, contain carbon dioxide.

Overview

The processes of this invention pertain to controlling the concentration of Adverse Component in an aqueous fermentation broth used for the bioconversion of syngas to product oxygenated organic compound.

Syngas Bioconversions

Anaerobic fermentation to produce product oxygenated organic compound uses a substrate (syngas) comprising at least one of (i) carbon monoxide and (ii) carbon dioxide and hydrogen, the latter being for the hydrogen conversion pathway. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier, reformer (steam, autothermal or partial oxidation). Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. These gases may have substantially different compositions than typical syngas, and may be essentially pure hydrogen or essentially pure carbon monoxide. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction.

The product oxygenated organic compounds produced in the processes of this invention will depend upon the microorganism or combination of microorganisms used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S Pat. No 5,173,429) and ATCC 55988 and 55989 (U.S Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA- 10522 described in U.S. Pat. No. 8,143,037.

Mixed cultures of anaerobic microorganisms can also be used for the bioconversions of syngas to product oxygenated organic compounds. See, for instance, U.S. patent applications Ser. No. 13/802,916, filed Mar. 14, 2013, entitled Method For Production Of N-Propanol And Other C3-Carbon Containing Products From Syngas By Symbiotic Arrangement Of C1-Fixing And C3-Producing Anaerobic Microorganism Cultures (Toby, et al.); Ser. No. 13/802,930, filed Mar. 14, 2013, entitled Method For Production Of N-Propanol And/Or Ethanol By Fermentation Of Multiple Substrates In A Symbiotic Manner (Enzein, et al.); Ser. No. 13/802,924, filed Mar. 14, 2013, entitled Method For Production Of N-Propanol And Other C3-Containing Products From Syngas Using Membrane Supported Bioreactor (Datta, et al.) and Ser. No. 13/802,905, filed Mar. 14, 2013, entitled Method For Production Of N-Propanol And Other C3-Containing Products From Syngas By Symbiotic Co-Cultures Of Anaerobic Microorganisms (Datta, et al.).

C1-fixing microorganisms include, without limitation, homoacetogens such as *Clostridium ljungdahlii*, *Clostridium autoethanogenum*, *Clostridium ragsdalei*, and *Clostridium coskatii*. Additional C1-fixing microorganisms include *Alkalibaculum bacchi*, *Clostridium thermoaceticum*, and *Clostridium aceticum*. Symbiotic C3-producing microorganisms capable of growing on ethanol and/or acetate as their primary carbon source include, but are not limited to, *Pelobacter propionicus*, *Clostridium neopropionicum*, *Clostridium propionicum*, *Desulfobulbus propionicus*, *Syntrophobacter wolinii*, *Syntrophobacter pfennigii*, *Syntrophobacter fumaroxidans*, *Syntrophobacter sulfatireducens*, *Smithella propionica*, *Desulfotomaculum thermobenzoicum* subspecies *thermosymbioticum*, *Pelotomaculum thermopropionicum*, and *Pelotomaculum schinkii*. Pathways for the production of product oxygenated organic compounds having three carbons include, but are not limited to, *Propionibacterium* species (*Propionibacterium acidipropionici*, *Propionibacterium acnes*, *Propionibacterium cyclohexanicum*, *Propionibacterium freudenreichii*, *Propionibacterium freudenreichii shermanii*, *Propionibacterium pentosaecum*) and several other anaerobic bacteria such as *Desulfobulbus propionicus*, *Pectinatus frisingensis*, *Pelobacter propionicus*, *Veillonella*, *Selenomonas*, *Fusobacterium*, *Bacteroides fragile*, *Prevotella ruminicola*, *Megasphaera elsdenii*, *Bacteroides vulgates*, and *Clostridium*, in particular *Clostridium propionicum*.

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

The aqueous broth is maintained under anaerobic fermentation conditions including a suitable temperature, say, between 25° C. and 60° C., frequently in the range of about 30° to 40° C. The conditions of fermentation, including the density of microorganisms and aqueous fermentation broth composition are preferably sufficient to achieve the sought conversion efficiency of hydrogen and carbon monoxide. The pH of the aqueous broth is acidic, preferably less than about 6.5, and often between about 4 and 6.5.

The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important. Preferably the feed gas is introduced into the bioreactor in the form of microbubbles. Often the microbubbles have diameters in the range of 0.01 to 0.5, preferably 0.02 to 0.3 millimeter.

The bioreactor assembly for syngas bioconversion may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors, including membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

The substrate depleted gas phase egressing from the aqueous fermentation broth will contain a small fraction of the hydrogen and carbon oxides introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

The bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Adverse Component

The Adverse Component that is contained in the aqueous fermentation broth for the syngas bioconversion can be from any source, including, but not limited to, an impurity in the feed gas and a metabolic product during the fermentation by the microorganism provided to produce the product oxygenated organic compound or by an adventitious microorganism contained in the fermentation broth.

The Adverse Component can be in a concentration such that the microorganism population for the bioconversion of syngas is substantially killed or is materially, adversely affected, either or both by inhibition and cell death. Alternatively, even if the Adverse Component does not adversely affect the microorganisms for the bioconversion of syngas, its build-up can adversely affect operation. For instance, the build-up may affect the ability to maintain a steady-state operation of a continuous process for making the product oxygenated organic compound.

The time of implementation of the processes of this invention thus can vary according to the cause and effect of the Adverse Component. Thus, the processes may be used continuously, intermittently or sporadically to address a build-up of the Adverse Component. This mode of implementation can be beneficial in those instances where higher concentrations of the Adverse Component can have an effect on the metabolic pathways used by the microorganism for the bioconversion of syngas which leads to an accelerated production of the Adverse Component.

The processes of this invention involve the recycle of at least a portion of the withdrawn fermentation broth after recovery of product oxygenated organic compound. The recovery of the product oxygenated organic compound can be by any suitable unit operation as discussed above. Preferably the solids contained in the withdrawn fermentation broth are substantially removed prior to the recycle of the fermentation broth.

Anaerobic Organic Bioconversion

A portion of the withdrawn fermentation broth after recovery of product oxygenated organic compound is subjected to anaerobic organic bioconversion to degrade at least a portion of the Adverse Component before recycling to the bioreactor assembly. Anaerobic organic bioconversion processes are well known, as are high rate anaerobic organic bioconversion processes.

The portion of the broth from product recovery that is subjected to the anaerobic organic bioconversion is sufficient that the concentration of the Adverse Component in the bioreactor assembly is maintained below that which unduly adversely affects the microorganisms. As used herein, the term control is broadly used to mean that this concentration of Adverse Component is below a pre-determined level and not necessarily that the concentration is maintained within a specific range. If desired, however, the processes of this invention can enable the concentration of Adverse Component to be maintained at steady state within a specified range.

In the process of the instant invention, the portion that is subjected to anaerobic organic bioconversion is modulated based on the concentration of the Adverse Component in the bioreactor assembly or in the fermentation broth that is recycled. If the concentration of the Adverse Component rises (trends upwardly), the portion shunted to the anaerobic organic bioconversion is increased above the prior flow rate. In some instances, the portion being subjected to anaerobic organic bioconversion is reduced in response to a downward trend in the concentration of the Adverse Component. Hence, a steady-state operation can be achieved. The target concentration of the Adverse Component can vary widely below that which unduly adversely affects the microorganisms. Frequently, the target concentration for a given co-produced oxygenated organic compound is between about 25 to 75 mass percent of that which results in an undue, adverse effect on the population of microorganisms. The level of shunting can be controlled manually or automatically based on a number of on-line inputs including but not limited to caustic (or other pH control chemicals) addition rate in the case where the Adverse Component comprises organic acid, on-line analyzers, or any number of other indicators of Adverse Component accumulation rate.

The anaerobic organic bioconversion may be conducted under any suitable metabolic conditions for the bioconversion of organic compound. In general, the processes are conducted under redox conditions such that the treated aqueous fermentation broth can be used for syngas bioconversion to oxygenated organic compound without the need for de-aeration or adjustment of redox potential. Many anaerobic organic bioconversion microorganisms are mesophilic and thus are operable within the temperature range used for the bioconversion of syngas. In these instances, the temperature of the aqueous fermentation broth is within the range of about 25° C. to about 40° C. The head pressure during the anaerobic organic bioconversion is not critical to the broad aspects of this invention, but usually is in the range of between about 50 and 1000 kPa. Since the aqueous fermentation broth is from the bioconversion of syngas, at least some nutrients, including micronutrients, typically will already be contained in the broth.

The pH of the aqueous fraction while being subjected to the anaerobic organic bioconversion is often in the range of about 6.5 to 8.5. In some instances, the depleted aqueous fraction being passed to the anaerobic organic bioconversion is at a lower pH. However, the bioconversion process itself tends to increase the pH. In many instances, the pH of the bioconversion product, which is only a portion of the recycling aqueous broth, need not be adjusted prior to being passed to the aqueous fermentation broth.

The anaerobic organic bioconversion may be conducted in a batch, semi-continuous or continuous mode. For a batch operation, the residence time should be sufficient to achieve the sought reduction in the undesired organic compound. For continuous operations, the residence time of the aqueous fermentation broth in the bioreactor should also be sufficient to achieve the sought reduction in the undesired organic compound.

Any suitable anaerobic bioreactor assembly may be used in the processes of this invention. The bioreactor assemblies for use in the processes of this invention include, but are not limited to, continuous stirred tank bioreactors and bioreactors for high rate anaerobic organic bioconversion as described above. One or more bioreactors may be used, and when two or more bioreactors are used, they may be in parallel or sequential operation. The bioreactor assembly can, but is not always required to, include heat exchangers; solids separation unit operations such as centrifuges, settling ponds and filters; gas/liquid separation unit operations; pumps; and equipment useful for monitoring and control of the bioreactor assembly.

Where the aqueous fermentation broth after being subjected to anaerobic organic bioconversion contains microorganisms, it is usually the case that the microorganisms are removed or denatured such that substantially no viable microorganisms are present when the syngas bioconversion is commenced. If the facility uses a centrifuge or other unit operation to separate solids from the fermentation broth, e.g., solids from the microorganisms used for the syngas bioconversion, the treated fermentation broth can be passed to the centrifuge or other unit operation. If the facility uses a sterilization unit operation to treat fermentation broth being recycled to the bioreactor assembly after product oxygenated organic compound recovery, the portion of the fermentation broth that was subjected to anaerobic organic bioconversion can also be directed to that sterilization unit operation.

In order to maintain a sought ionic balance in the fermentation broth it is usually necessary to purge a portion of the fermentation broth, and this purge is generally from the recycling aqueous fermentation broth after recovering product oxygenated organic compound. In one preferred embodiment of this invention, the purge is from the aqueous broth that has been treated by the anaerobic organic bioconversion, and thus the purge would have low, if any, organic carbon content.

Drawings

A general understanding of the invention and its application may be facilitated by reference to FIG. 1. FIG. 1 is a schematic depiction of an apparatus generally designated as 100 suitable for practicing processes in accordance with this invention. FIG. 1 omits minor equipment such as pumps, compressors, valves, instruments, the exchangers and other devices the placement of which and the operation thereof are well known to those practiced in chemical engineering. FIG. 1 also omits ancillary unit operations. The processes and operation of FIG. 1 will be described in the context of the recovery and production of ethanol. The process is readily adaptable to processes for making other oxygenated organic compounds such as acetic acid, propanol and butanol.

Apparatus contains fermentation reactor 102 which is adapted to hold an aqueous fermentation broth and microorganisms for bioconverting syngas to ethanol. Fermentation reactor 102 is adapted to be operated on a continuous basis. The syngas is provided to bioreactor 102 via line 104. An off gas, which typically contains nitrogen, methane, and unreacted hydrogen, carbon dioxide and carbon monoxide, is withdrawn from bioreactor 102 via line 106. A portion of the aqueous fermentation broth in fermentation reactor 102 is withdrawn via line 108 and is passed to distillation assembly 110. Distillation assembly 110 separates ethanol from the aqueous phase and provides an ethanol rich product which is withdrawn via line 112. The heat in the distillation assembly 110 kills the microorganisms used for the bioconversion of syngas. A bottoms stream containing solids from the microorganisms and proteins precipitated from solution in an aqueous phase is passed via line 114 to a solids separation unit operation 116, which for purposes of discussion is a centrifuge. The bottoms stream also contains higher boiling organic compounds such as acetates. A solids-rich stream is removed from centrifuge 116 via line 118, and the solids-rich stream can be processed for waste recovery, e.g., in an anaerobic digester. Centrifuge 116 also provides an aqueous stream which exits via line 120 and can be redirected to fermentation reactor 102 via line 122. Line 122 is shown as directing the broth to sterilizing unit operation 140 which for purposes of discussion is a steam heated tank to increase the temperature of the fermentation broth sufficiently to effect sterilization. The sterilized broth is returned to fermentation reactor 102 via line 142.

Line 120 from centrifuge 116 is capable of directing the aqueous stream to either line 122 for return to fermentation reactor 102 or to line 124 to be passed to high rate anaerobic bioreactor 126. Anaerobic bioreactor 126 contains microorganisms that anaerobically degrade acetate and other oxygenated organic compounds present in the aqueous stream. Off-gases generated by the anaerobic organic bioconversion exit anaerobic digester 126 via line 130. These gases comprise methane and carbon dioxide and can be used as energy source. The aqueous stream, after being subjected to the anaerobic organic bioconversion, is withdrawn from anaerobic bioreactor 126 via line 128 and is passed to solids separation unit 134. As shown, a liquid purge is removed from line 128 via line 132. Advantageously, the liquid purge has a substantially reduced carbon content.

A solids-containing purge stream from solids separation unit 134 exits via line 138 and can be sent to a waste treatment facility or all or a portion of the purge stream can be returned to anaerobic bioreactor 126 to assist in maintaining a desired population of anaerobic organic bioconversion microorganisms.

A stream having a reduced solids content is withdrawn from solids separation unit operation 134 via line 136 which can direct a substantially solids-free broth to sterilizing unit operation 140. Sterilizing unit operation 140 is optional. The stream is then returned to fermenter 102 via line 142.

It is claimed:

1. A process for controlling the concentration of at least one co-produced oxygenated organic compound in an anaerobic, aqueous fermentation broth used for bioconverting a gas substrate comprising carbon monoxide, hydrogen and carbon dioxide in the aqueous fermentation broth which contains microorganisms suitable for converting said gas substrate to product oxygenated organic compound, comprising:

a. continuously contacting said gas substrate with said aqueous fermentation broth in a bioreactor assembly, said aqueous fermentation broth being under acidic, anaerobic fermentation conditions, to bioconvert said gas substrate to oxygenated organic compounds and provide at least one product oxygenated organic compound-containing broth and a depleted gas phase, said anaerobic fermentation conditions also producing a co-produced oxygenated organic compound;

b. continuously withdrawing the depleted gas phase from said aqueous fermentation broth;

c. continuously or intermittently withdrawing a portion of said aqueous fermentation broth for recovery of said at least one product oxygenated organic compound, said withdrawal being sufficient to maintain the product oxygenated organic compound in said aqueous fermentation broth below a concentration that unduly adversely affects the microorganisms in the bioreactor assembly;

d. continuously separating said at least one product oxygenated organic compound from the withdrawn portion of said aqueous fermentation broth to provide at least one fraction rich in said at least one product oxygenated organic compound and a depleted aqueous fraction containing said at least one co-produced oxygenated organic compound, the depleted aqueous fraction having a first aqueous portion and a second aqueous portion;

e. continuously recycling the first aqueous portion of the depleted aqueous fraction containing said at least one co-produced oxygenated organic compound to the aqueous fermentation broth in the bioreactor assembly;

f. continuously or intermittently subjecting the second aqueous portion of the depleted aqueous fraction to anaerobic organic bioconversion to form a bioconverted second aqueous portion, wherein the second aqueous portion of the depleted aqueous fraction subjected to anaerobic organic bioconversion includes a portion of said at least one co-produced oxygenated organic compound and the anaerobic organic bioconversion is sufficient to maintain the concentration of the at least one co-produced oxygenated organic compound below that which unduly adversely affects the microorganisms in the bioreactor assembly; and g. directing the bioconverted second aqueous portion back to the aqueous fermentation broth in the bioreactor assembly of step (a).

2. The process of claim 1 wherein the product oxygenated organic compound comprises at least one alcohol.

3. The process of claim 2 wherein the at least one co-produced oxygenated organic compound comprises a lower carboxylate.

4. The process of claim 3 wherein the lower carboxylate comprises acetate anion.

5. The process of claim 1 wherein the anaerobic organic bioconversion is a high rate anaerobic organic bioconversion.

6. The process of claim 5 wherein the anaerobic organic bioconversion is a membrane-type anaerobic organic bioconversion.

7. The process of claim 5 wherein the anaerobic organic bioconversion is an attached growth-type anaerobic bioconversion.

8. The process of claim 1 wherein the continuously or intermittently subjecting the second aqueous portion of the depleted aqueous fraction to anaerobic organic bioconversion controls concentration of the at least one co-produced oxygenated organic compound within about 10 and 75 percent of that concentration which would adversely affect the microorganisms.

9. The process of claim 1 wherein less than about 50 volume percent of the depleted aqueous fraction is subjected to anaerobic organic bioconversion in step (f).

10. The process of claim 9 wherein between about 5 and 25 volume percent of the depleted aqueous fraction is subjected to anaerobic organic bioconversion in step (f).

11. The process of claim 1 wherein a biogas is generated in step (f).

12. The process of claim 11 further comprising passing at least a portion of the biogas to the aqueous fermentation broth of step (a).

13. The process of claim 11 further comprising reforming at least a portion of the biogas as to produce syngas.

14. The process of claim 11 further comprising using at least a portion of the biogas an energy source.

15. The process of claim 1 further comprising purging at least a portion of the depleted aqueous fraction to maintain an ionic balance in the aqueous fermentation broth and the purge is taken from the depleted aqueous fraction that has been subjected to the anaerobic organic bioconversion of step (f).

16. The process of claim 1 wherein the pH of the depleted aqueous fraction being subjected to anaerobic organic bioconversion is between about 6.5 and 8.5.

* * * * *